United States Patent
Tomita et al.

(10) Patent No.: US 6,973,233 B1
(45) Date of Patent: Dec. 6, 2005

(54) VARIABLE-WAVELENGTH OPTICAL OUTPUT DEVICE

(75) Inventors: Norifumi Tomita, Hamamatsu (JP); Yoshio Isobe, Hamamatsu (JP); Hirotoshi Terada, Hamamatsu (JP); Yoshinori Mizuguchi, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 179 days.

(21) Appl. No.: 10/089,866

(22) PCT Filed: Oct. 6, 2000

(86) PCT No.: PCT/JP00/06998

§ 371 (c)(1),
(2), (4) Date: Apr. 5, 2002

(87) PCT Pub. No.: WO01/25736

PCT Pub. Date: Apr. 12, 2001

(30) Foreign Application Priority Data

Oct. 7, 1999 (JP) .............................. P1999-286902

(51) Int. Cl.$^7$ .............................. G02B 6/26; G01J 3/18

(52) U.S. Cl. ........................................ 385/31; 356/334

(58) Field of Search .............................. 356/308, 328, 356/326, 332, 334

(56) References Cited

U.S. PATENT DOCUMENTS

| | | | | |
|---|---|---|---|---|
| 4,225,233 A | * | 9/1980 | Ogan | ........................ 356/308 |
| 4,669,878 A | * | 6/1987 | Meier | ........................ 356/319 |
| 5,455,674 A | * | 10/1995 | Purcell | ........................ 356/318 |

FOREIGN PATENT DOCUMENTS

| | | |
|---|---|---|
| EP | 0 540 966 A1 | 5/1993 |
| JP | 1-223929 | 9/1989 |
| JP | H1-136431 | 9/1989 |
| JP | H6-61489 | 8/1994 |
| JP | 7-104397 | 4/1995 |
| JP | 9-179002 | 7/1997 |
| JP | 5-167159 | 7/2003 |

* cited by examiner

*Primary Examiner*—Joseph Williams
*Assistant Examiner*—Peter Macchiarolo
(74) *Attorney, Agent, or Firm*—Morgan Lewis & Bockius LLP (57) ABSTRACT

In a wavelength-variable light outputting apparatus, a diffraction grating 8 and a shielding member 11 which make wavelength and light quantity variable are attached to galvanometric scanners 12, 13, respectively, and the latter are swung, whereby the wavelength can be made variable at a high speed while in a state where the light quantity is kept constant. Such an apparatus is useful for capturing a fluorescent image of a biological sample in particular. By way of the shielding member 11, light is made incident on the optical fiber 10 and is outputted therefrom, whereby a biological sample SM can effectively be irradiated with light.

6 Claims, 6 Drawing Sheets

VARIABLE-WAVELENGTH OPTICAL OUTPUT DEVICE

TECHNICAL FIELD

The present invention relates to a wavelength-variable light outputting apparatus for irradiating an object with light whose wavelength is made variable.

BACKGROUND ART

A conventional wavelength-variable light outputting apparatus is disclosed in Japanese Patent Application Laid-Open No. HEI 1-223929. In this apparatus, light outputted from a light source is made incident on an optical filter rotator having three colors of red (R), green (G), and blue (B), whereby light having a desirable wavelength is outputted therefrom. For controlling color light quantities independently from each other, it will be sufficient if a plurality of liquid crystal filters, ND filters having respective light attenuation ratios different from each other, and the like are arranged on the output side of each optical filter and switched therebetween.

DISCLOSURE OF THE INVENTION

The conventional wavelength-variable light outputting apparatus can be used for observing biological samples. Namely, when a fluorescence-labeled biological sample disposed under a microscope is irradiated with monochromatic light having a selected wavelength as pumping light, fluorescence occurs from the biological sample. Thus generated fluorescence can be captured as a fluorescent image of the biological sample.

Since the transmission or absorption wavelength band of a material constituting the sample varies depending on the kind of material, a sample image reflecting the material constituting the sample can be obtained if the sample image is captured with variable wavelengths.

Since a plurality of wavelengths of light are necessary depending on kinds of fluorescence labels and sample-constituting materials, it is desirable that wavelengths be rapidly changed and switched in order to shorten the measurement time. When combining images obtained upon irradiation with a plurality of wavelengths, in particular, it is preferred that the irradiation light quantity be constant from the viewpoint of utility in analysis.

However, wavelength sweeping cannot be carried out at a high speed in the above-mentioned conventional apparatus. Namely, the light from the light source has a wavelength distribution, so that its light quantity differs from wavelength to wavelength, whereby it is necessary for a plurality of optical filters and ND filters provided independently from each other to rotate and move at a high speed in order to make wavelengths variable while maintaining a constant light quantity. However, continuous wavelength sweeping requires a number of filters, each of which has a large mass, so that a driving apparatus moving such a structure while controlling its position can operate only at a relatively low speed.

In view of the problem mentioned above, it is an object of the present invention to provide a wavelength-variable light outputting apparatus which can make wavelengths variable at a high speed while controlling light quantities.

For overcoming the above-mentioned problem, the present invention provides a wavelength-variable light outputting apparatus comprising a light source outputting light having a plurality of wavelengths, a swinging first galvanometric scanner provided with spectroscopic means for spectrally dividing the light outputted from the light source, a swinging second galvanometric scanner provided with a shielding or reflecting member adapted to block or reflect at least a part of light outputted from the spectroscopic means, and an optical fiber disposed at a position where light outputted from the spectroscopic means can be made incident by way of the shielding or reflecting member.

The light outputted from the light source is fed into spectroscopic means such as a diffraction grating or prism. Since the spectroscopic means spectrally divides the light outputted from the light source, the emitting direction of a specific wavelength component among thus divided light components can be deflected by swinging the first galvanometric scanner. This specific wavelength component is made incident on the shielding or reflecting member, whereby a part thereof is blocked or reflected. Since such a member is provided with the second galvanometric scanner, the transmission light quantity or reflecting direction of the specific wavelength component varies when the second galvanometric scanner is swung.

Since the optical fiber is disposed at a position where light outputted from the spectroscopic means can be made incident by way of the shielding or reflecting member, the quantity of light finally incident on the optical fiber can vary if the transmission light quantity is made variable by the shielding member, whereas, due to the fact that the input end face of the optical fiber has a core with a finite diameter, the quantity of light finally entering the core of the optical fiber will vary if the reflecting direction is made variable by the reflecting member.

Thus, since galvanometric scanners which can swing at a high speed are provided with the spectroscopic means and the shielding or reflecting member, this wavelength-variable light outputting apparatus can select a specific wavelength component at a high speed and make its light quantity variable at a high speed.

Preferably, this wavelength-variable light outputting apparatus comprises storage means for storing respective swinging angles of the first and second galvanometric scanners and a relationship between the wavelength and quantity of light outputted from the optical fiber in response to a combination of the swinging angles, input means for inputting information concerning the wavelength and quantity of light to be outputted from the optical fiber, and control means for reading out the above-mentioned relationship from the storage means according to the information fed into the input means and controlling the swinging angles of the first and second galvanometric scanners in response to the relationship.

The storage means such as a memory stores therein respective swinging angles of the first and second galvanometric scanners and a relationship between the wavelength and quantity of light outputted from the optical fiber in response to a combination of the swinging angles. When information concerning the wavelength and quantity of light to be outputted from the optical fiber is fed into the input means such as a keyboard, the control means reads out the above-mentioned relationship from the storage means according to the information fed into the input means, and controls the swinging angles in response to this relationship. Namely, the wavelength and quantity of light outputted from the optical fiber can definitely be determined according to a combination of swinging angles, whereby desirable light can be outputted from the optical fiber based on the input to the input means alone.

Also, this wavelength-variable light outputting apparatus may comprise control means for changing the wavelength of light outputted from the optical fiber by changing a swinging angle of the first galvanometric scanner and changing a swinging angle of the second galvanometric scanner such that the quantity of the wavelength of light fed to the shielding or reflecting member in response to the swinging angle of the first galvanometric scanner and The ratio of incidence of light incident on the optical fiber in response to the swinging angle of the second galvanometric scanner form a fixed product therebetween.

When the swinging angle of the first galvanometric scanner is changed, the wavelength of light outputted from the optical fiber changes. The quantity of the wavelength of light fed to the shielding or reflecting member varies depending on this swinging angle. In order for the light finally outputted from the optical fiber to become constant, it will be sufficient if the quantity of the wavelength of light fed to the shielding or reflecting member in response to the swinging angle of the first galvanometric scanner and the ratio of incidence of the light incident on the optical fiber in response to the swinging angle of the second galvanometric scanner form a fixed product therebetween.

The control means changes the swinging angle of the second galvanometric scanner so as to satisfy this relationship. If the swinging angle of the second galvanometric scanner for satisfying such a relationship is determined beforehand by use of a calculation or lookup table system, the time required for determining it can be shortened, whereby the wavelength can be made variable at a higher speed under a constant light quantity. However, the swinging angle of the second galvanometric scanner may also be determined sequentially in response to the swinging angle of the first galvanometric scanner.

BEST MODES FOR CARRYING OUT THE INVENTION

In the following, wavelength-variable light outputting apparatus in accordance with embodiments will be explained. In the explanation, constituents identical to each other will be referred to with numerals identical to each other without repeating their overlapping descriptions.

Figure 1:
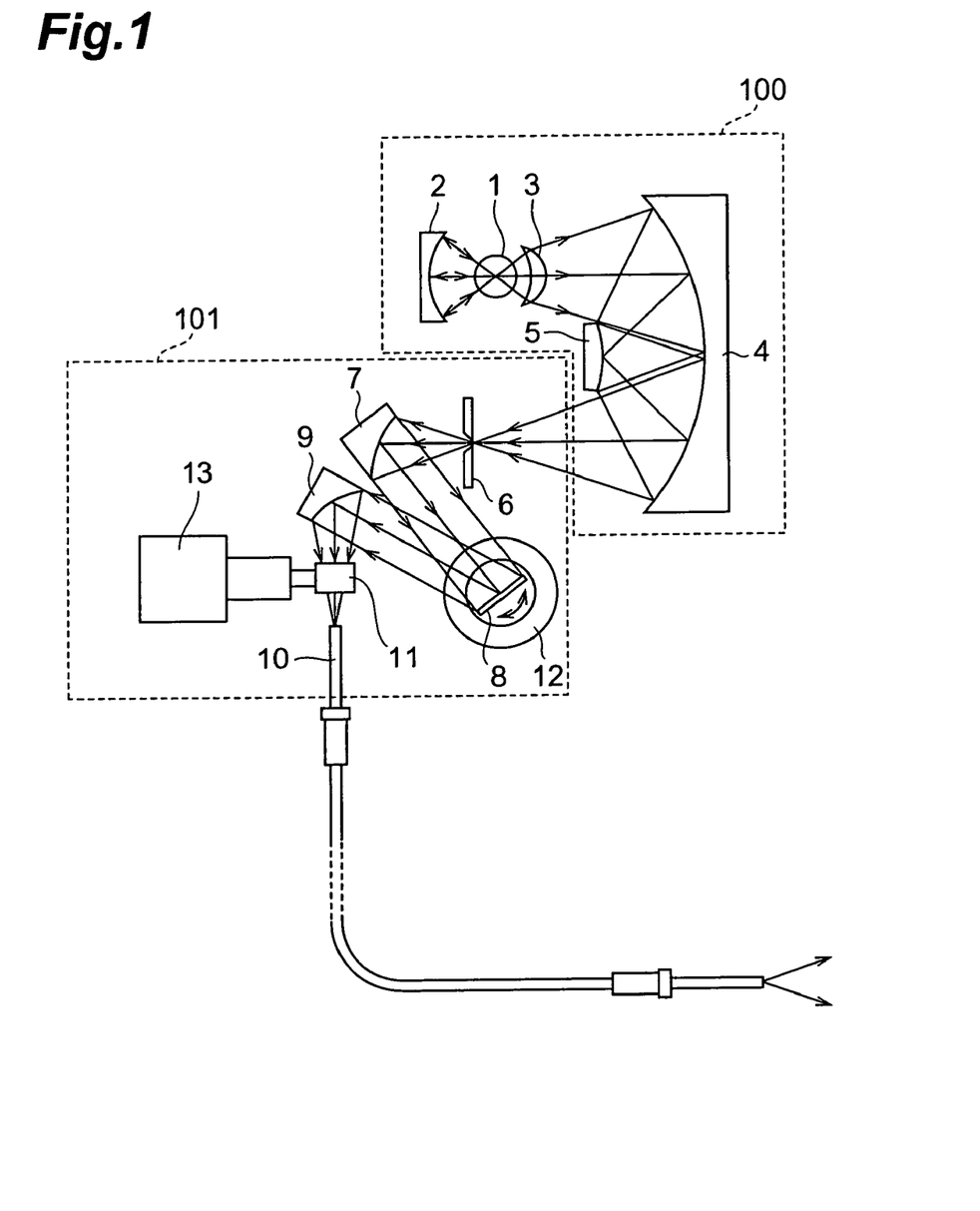
FIG 1 is an explanatory view showing the configuration of a wavelength-variable light outputting apparatus.

FIG. 1 is an explanatory view showing the configuration of a wavelength-variable light outputting apparatus. This wavelength-variable light outputting apparatus is constituted by a light source section 100 for emitting light, and a spectroscopic section 101 for spectrally dividing the emitted light while adjusting the light quantity thereof. This will be explained in more detail.

The wavelength-variable light outputting apparatus comprises a light source 1 such as an Xe lamp. Though the light outputted from the light source 1 diverges in all directions, it is reflected to the front side of the light source 1 by a small concave reflecting mirror 2 disposed so as to face the light source 1 on the back side (left side in the drawing) thereof, and is made incident on a large concave reflecting mirror 4 by way of a lens 3 together with the light directly emitted from the light source 1 to the front side.

A convex reflecting mirror 5 is disposed near the center of curvature of the concave reflecting mirror 4, so that the light reflected by the concave reflecting mirror 4 is reflected again toward the concave reflecting mirror 4. The light reflected twice by the concave reflecting mirror 4 is converged at a position where an entrance slit 6 is disposed, and passes through the slit 6. The light emitted from the slit 6 is collimated by an off-axis parabolic mirror 7, so as to irradiate a diffraction grating (spectroscopic means) 8 which is rotatably movable.

The light irradiated on the diffraction grating 8 is spectrally divided into separate wavelength components which are made incident on the off-axis parabolic mirror 9, and are converged thereby onto an input end face of an optical fiber 10. A rotatably movable shielding member 11 is disposed in an optical path between the off-axis parabolic mirror 9 and the optical fiber 10. The light converged onto the input end face of the optical fiber 10 passes through the optical fiber 10, so as to be outputted from the output end face thereof.

The diffraction grating 8 is attached to a first galvanometric scanner 12, whereas the first galvanometric scanner 12 swings the diffraction grating 8 while using an axis perpendicular to the optical axis of light incident on the diffraction grating 8 as the axis of swinging. When the diffraction grating 8 is swung by driving the first galvanometric scanner 12, the advancing direction of a specific wavelength component outputted from the diffraction grating 8 is deflected, whereby the light fed to the optical fiber 10 changes its wavelength.

The light-shielding member 11 disposed in the optical path leading to the optical fiber 10 is attached to a second galvanometric scanner 13, which swings the light-shielding member 11 while using an axis perpendicular to the optical axis of light incident on the optical fiber 10 as the axis of swinging. When the second galvanometric scanner 13 is driven so as to swing the light-shielding member 11, the light incident on the optical fiber 10 is partly blocked by the shielding member 11, whereby the quantity of light fed into the optical fiber 10 changes.

Figure 2A:
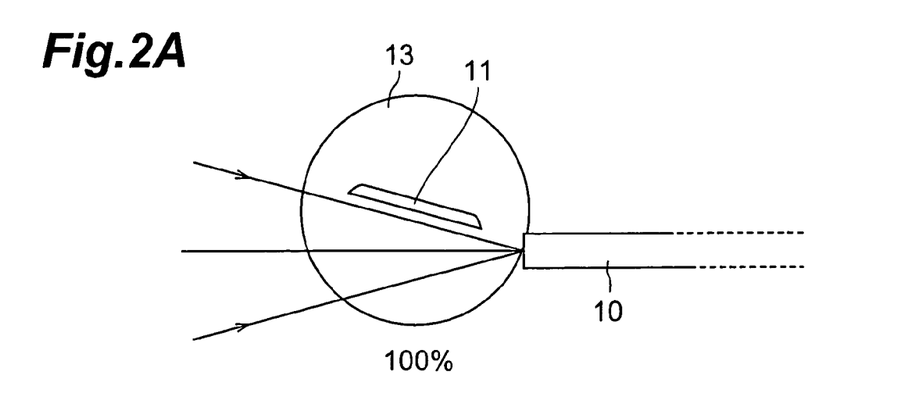
FIGS. 2A, 2B, and 2C are explanatory views showing relationships between positions of a shielding member 11 and light incident on an optical fiber 10.
Figure 2B:
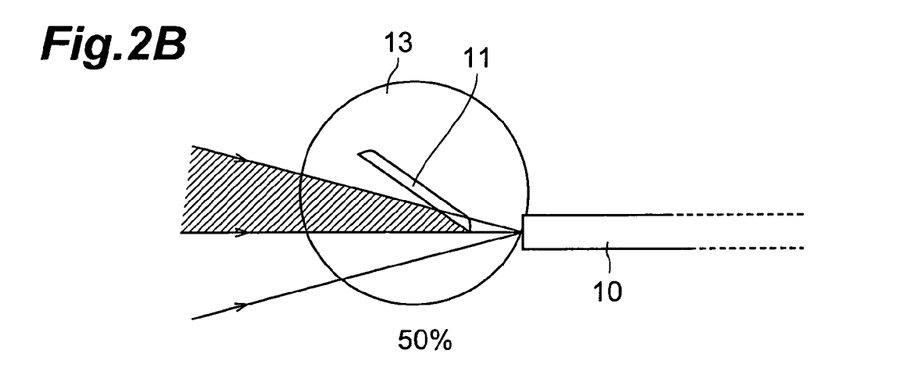
Figure 2C:
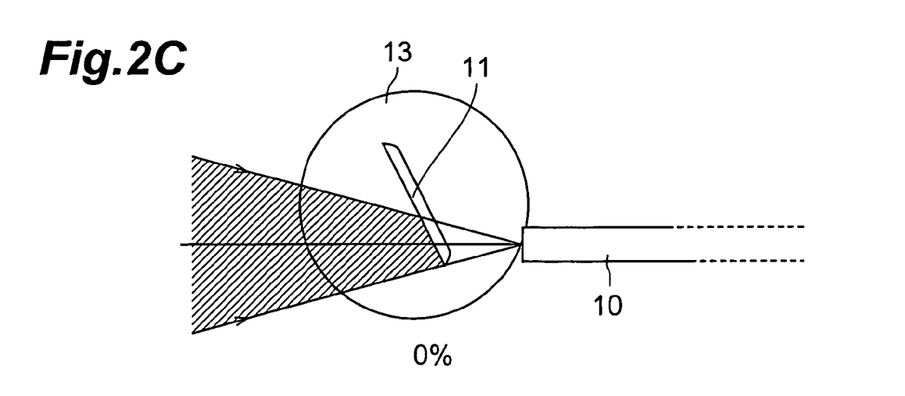

FIGS. 2A, 2B, and 2C are explanatory views showing relationships between positions of the shielding member 11 and light incident on the optical fiber 10. As shown in these drawings, the swinging axis of the second galvanometric scanner 13 does not intersect the optical axis of the optical fiber 10, but is positioned outside the effective diameter, perpendicular to the optical axis, of the light converged onto the input end face of the optical fiber 10.

When the whole light-shielding member 11 is positioned outside the convergent light as shown in FIG. 2A, 100% of the convergent light enters the optical fiber 10 (incidence ratio β=100%).

When an outer edge of the light-shielding member 11 on the optical axis side is positioned on the optical axis of the convergent light as shown in FIG. 2B, 50% of the convergent light enters the optical fiber 10 (incidence ratio β=50%).

When the whole light-shielding member 11 is positioned within the optical path of the convergent light as shown in FIG. 2C, 0% of the convergent light enters the optical fiber 10 (incidence ratio β=0%).

Thus, the swinging angle θ2 of the light-shielding member 11 and the incidence ratio β of convergent light correspond to each other one to one. Similarly, the swinging angle θ1 of the diffraction grating 8 and the emission angle of output light from the diffraction grating 8, i.e., the advancing direction of a specific wavelength component, correspond to each other one to one. The diffraction grating 8 can be replaced by a prism which spectrally divides light in a similar fashion.

Figure 3:
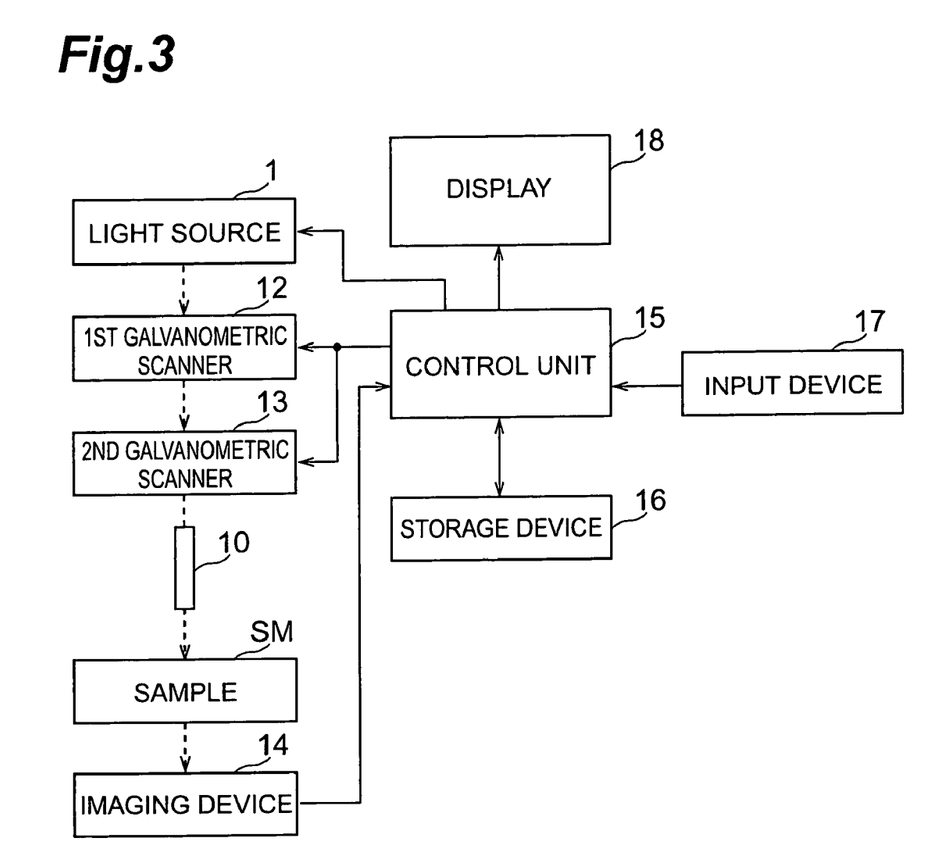
FIG. 3 is a block diagram showing a system configuration of a fluorescent image capturing apparatus using the above-mentioned wavelength-variable light outputting apparatus.

FIG. 3 is a block diagram showing a system configuration of a fluorescent image capturing apparatus using the above-mentioned wavelength-variable light outputting apparatus. This fluorescent image capturing apparatus combines the wavelength-variable light outputting apparatus with an imaging device 14. Namely, in this apparatus, a fluorescence-labeled biological sample SM is irradiated with light emitted from the optical fiber 10, and a fluorescent image of the sample generated upon the irradiation is captured by the imaging device 14.

This diagram shows a control unit (control means) 15 for controlling the light source 1 and scanners 12, 13 in the wavelength-variable light outputting apparatus; a storage device (storage means) 16 such as a memory for storing control conditions effected by the control unit 15, an input device (input means) 17 such as a keyboard with which an operator inputs operations of the wavelength-variable light outputting apparatus, and a display 18 for displaying the information about input to the input device 17 and the image captured by the imaging device 14.

The storage device 16 in this apparatus stores the respective swinging angles θ1, θ2 of the first and second galvanometric scanners 12, 13 and the relationship ((θ1, θ2)=(λ, E)) between the wavelength λ and quantity E of light outputted from the optical fiber 10 in response to the combination of the swinging angles θ1, θ2. Here, the wavelength refers to the center wavelength.

Information (λ, E) concerning the wavelength λ and quantity E of light to be outputted from the optical fiber 10 is fed into the input device 17.

According to the information (λ, E) fed into the input device 17, the control unit 15 reads out the relationship ((λ, E)=(λ1, λ2)) from the storage device 16, and controls the swinging angles λ1, λ2 of the first and second galvanometric scanners 12, 13 in conformity to this relationship. Namely, (θ1, θ2) is determined so as to match target (λ, E), and the first and second galvanometric scanners 12, 13 are driven so as to attain (λ1, λ2). Thereafter, the control unit 15 turns on the light source 1 or carries out the driving while turning on the light source 1.

Namely, this apparatus can definitely determine the wavelength λ and quantity E of light to be outputted from the optical fiber 10 according to the combination of swinging angles (θ1, θ2), thereby being able to output desirable light from the optical fiber 10 in response to the input to the input device 17 alone.

The following table shows the center wavelength (nm) and half width (nm) of light emitted from the optical fiber 10 in the case where the quantity of light (output) (mW) is made variable at each of wavelengths λ of 380 nm, 500 nm, and 650 nm.

| λ = 380 nm | | | λ = 500 nm | | | λ = 650 nm | | |
|---|---|---|---|---|---|---|---|---|
| output (mW) | center wavelength (nm) | half width | output (mW) | center wavelength (nm) | half width | output (mW) | center wavelength (nm) | half width |
| 2.88 | 380.1 | 15.5 | 3.32 | 500.2 | 14.4 | 1.25 | 650.0 | 13.7 |
| 2.61 | 380.1 | 15.4 | 3.00 | 500.2 | 14.6 | 1.12 | 650.0 | 13.7 |
| 2.32 | 380.1 | 15.6 | 2.67 | 500.2 | 14.7 | 1.00 | 650.0 | 13.7 |
| 2.02 | 380.1 | 15.5 | 2.32 | 500.2 | 14.5 | 0.88 | 650.0 | 13.7 |
| 1.74 | 380.1 | 15.5 | 1.98 | 500.2 | 14.6 | 0.75 | 650.0 | 13.7 |
| 1.43 | 380.1 | 15.5 | 1.65 | 500.2 | 14.3 | 0.62 | 650.0 | 13.5 |
| 1.16 | 380.1 | 15.2 | 1.32 | 500.2 | 14.3 | 0.50 | 650.0 | 13.5 |
| 0.87 | 380.1 | 15.1 | 1.00 | 500.2 | 14.1 | 0.37 | 650.0 | 13.0 |
| 0.57 | 380.1 | 15.0 | 0.66 | 500.7 | 13.8 | 0.25 | 650.0 | 12.5 |
| 0.25 | 380.1 | 14.3 | 0.29 | 501.2 | 13.1 | 0.11 | 650.0 | 11.7 |

As can be seen from this table, it is verified in this apparatus that changes in light quantity do not alter the center wavelength, and hardly vary the half width.

While altering the output light wavelength λ from the optical fiber 10 by changing the swinging angle θ1 of the first galvanometric scanner 12, the swinging angle θ2 of the second galvanometric scanner 13 may be changed such that the product of the light quantity e of the wavelength of light fed to the shielding member 11 or a reflecting member 11', which will be explained later, in response to the swinging angle θ1, and the ratio of incidence β of light incident on the optical fiber 10 in response to the swinging angle θ2 of the second optical fiber 10, (e×β)=E, becomes constant.

When the swinging angle θ1 of the first galvanometric scanner 12 is altered, the output light wavelength λ from the optical fiber 10 changes. Since the light emitted from the light source 1 has a wavelength distribution, the light quantity e of the wavelength of light fed to the shielding or reflecting member 11, 11' in response to the swinging angle θ1 varies. For making the quantity E of light finally outputted from the optical fiber 10 constant, it will be sufficient if the light quantity e of the wavelength of light fed to the shielding or reflecting member 11, 11' in response to the swinging angle θ1 of the first galvanometric scanner 12, and the incidence ratio β of the light incident on the optical fiber 10 in response to the swinging angle θ2 of the second galvanometric scanner 13 form a fixed product therebetween.

The control unit 15 changes the swinging angle θ2 of the second galvanometric scanner 13 so as to satisfy the above-mentioned relationship. If the swinging angle θ2 of the second galvanometric scanner 13 for satisfying such a relationship is determined beforehand by use of a calculation or lookup table system, the time required for determining it can be shortened, whereby the wavelength can be made variable at a higher speed under a constant light quantity. However, the swinging angle θ2 of the second galvanometric scanner 13 can be determined sequentially in response to the swinging angle θ1 of the first galvanometric scanner 12.

Finally, the light quantity control using the reflecting member 11' will be explained.

Figure 4:
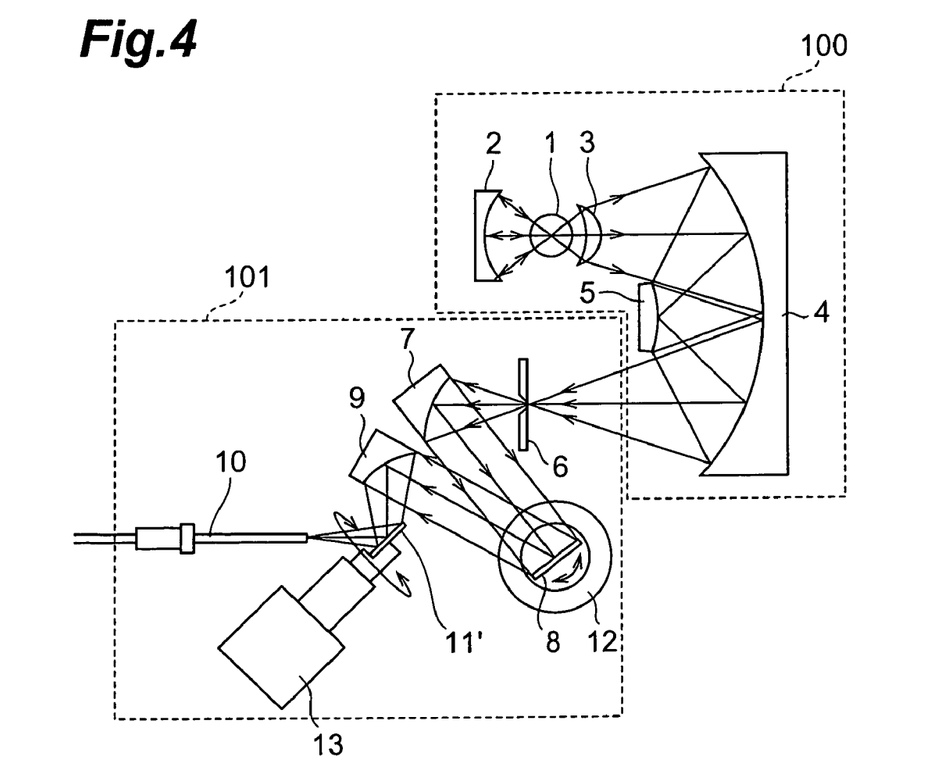
FIG. 4 is an explanatory view showing the configuration of the wavelength-variable light outputting apparatus in accordance with another embodiment.

FIG. 4 is an explanatory view showing the configuration of the wavelength-variable light outputting apparatus in accordance with another embodiment. This apparatus differs from that of the above-mentioned one only in that the member provided in the second galvanometric scanner 2 is not the shielding member 11 but the reflecting member 11', and that the swinging axis of the second galvanometric scanner 13 is disposed oblique with respect to the optical axis of light incident on the reflecting member 11'.

Namely, a specific wavelength component in the light spectrally divided by the diffraction grating 8 is converged by an off-axis parabolic mirror 9, and is reflected by the reflecting member 11' disposed in the optical path between the off-axis parabolic mirror 9 and the optical fiber 10, so as to be converged onto the input end face F of the optical fiber 10 (S being a spot of converged light). Therefore, due to the swinging of the second galvanometric scanner 13, the position of light-collecting spot S moves, whereby the light incidence ratio β to the optical fiber changes.

Figure 5A:
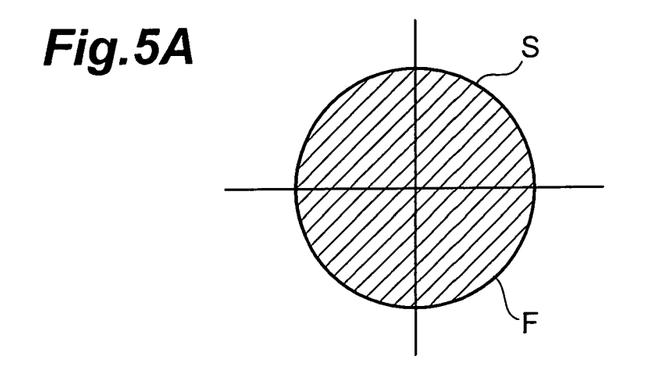
FIGS. 5A, 5B, and 5C are explanatory views showing positional relationships between the input end face (core) F of the optical fiber 10 and a light-collecting spot S.
Figure 5B:
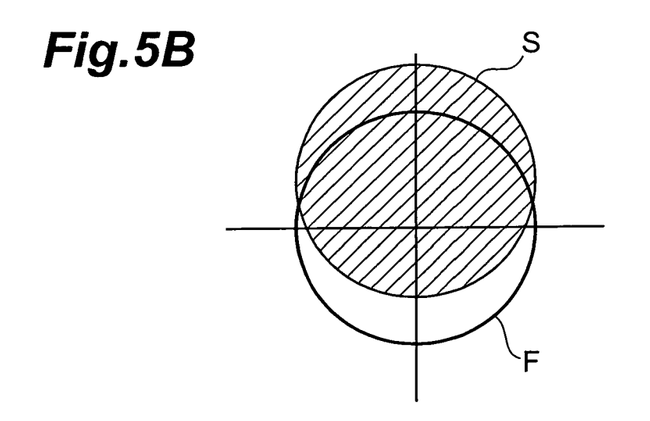
Figure 5C:
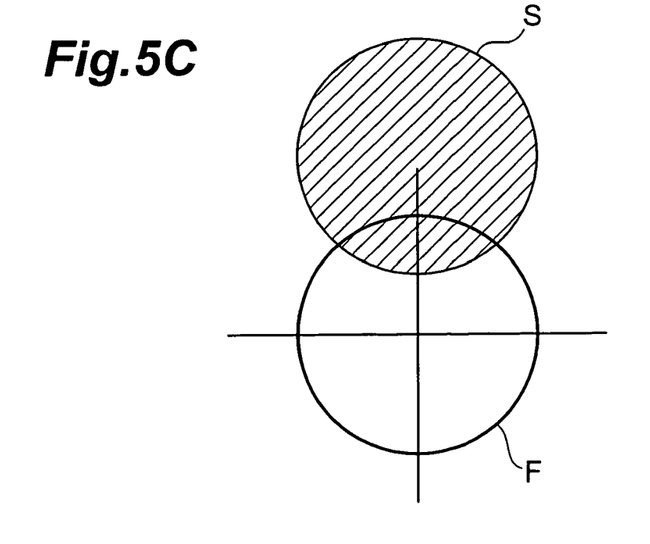

FIGS. 5A, 5B, and 5C are explanatory views showing positional relationships between the input end face (core) F of the optical fiber 10 and the light-collecting spot S.

When the position of converged light spot S and the position of optical fiber end face F coincide with each other, i.e., their centers of gravity coincide with each other, so that the spot S and the end face F completely overlay each other as shown in FIG. 5A, the light incidence ratio β is 100%.

When the position of converged light spot S and the position of optical fiber end face F slightly deviate from each other, i.e., their centers of gravity shift from each other, so that the spot S and end face F partly overlap each other as shown in FIGS. 5B and 5C, the light incidence ratio β is greater than 0% but smaller than 100%. When no overlap exists, the light incidence ratio β is 0%.

Thus, in this embodiment, the second galvanometric scanner 13 is driven so as to swing the reflecting member 11', whereby the light incidence ratio β can be changed.

The quantity of light outputted from the optical fiber 10 in the wavelength-variable light outputting apparatus in the former embodiment was measured at a wavelength of 380 nm. Here, for verifying whether high-speed variation was possible or not, the light incidence ratio β was changed by driving the second galvanometric scanner 13.

Figure 6:
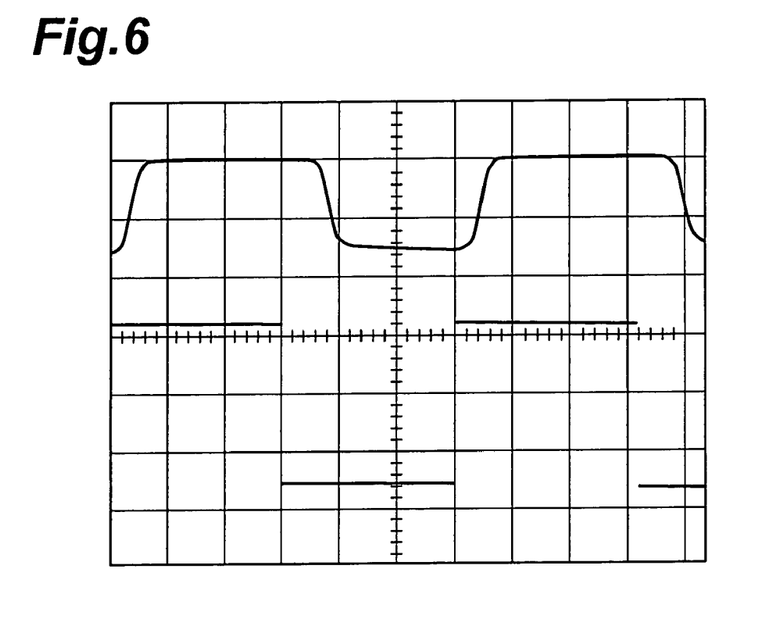
FIG. 6 is a graph showing the change in quantity (intensity) of light outputted from the optical fiber 10 with time when light incidence ratio β was changed from 100% to 50%.

FIG. 6 is a graph showing the change in quantity (intensity) of light outputted from the optical fiber 10 with time when the light incidence ratio β was changed from 100% to 50%.

Figure 7:
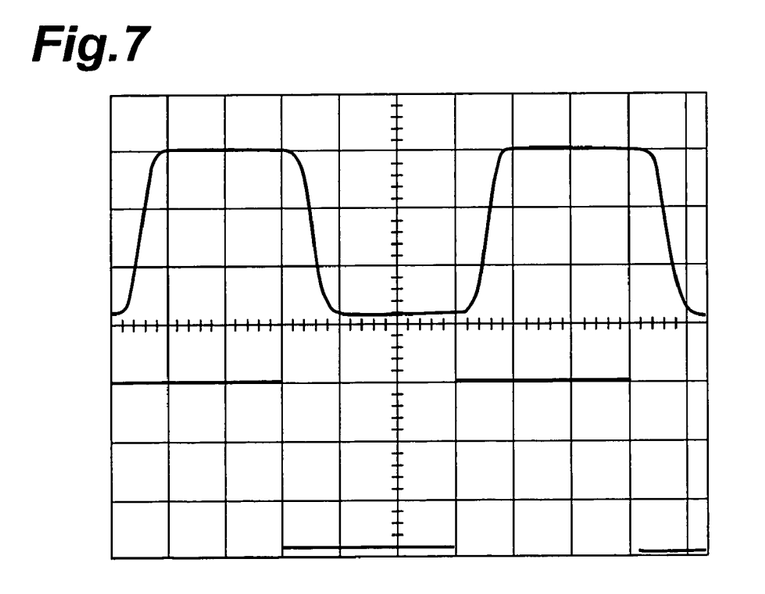
FIG. 7 is a graph showing the change in quantity (intensity) of light outputted from the optical fiber 10 with time when light incidence ratio β was changed from 100% to 0%.

FIG. 7 is a graph showing the change in quantity (intensity) of light outputted from the optical fiber 10 with time when the light incidence ratio β was changed from 100% to 0%. These light quantities were detected by a photodiode.

In both graphs, signals in the upper half indicate the quantity of light (2 V/div), whereas signals in the lower half indicate driving signals fed into the second galvanometric scanner 13 (5 V/div), with a temporal axis of 2 ms/div. These graphs have proved that changes in light quantity can be completed in a short time of 2 ms or less after the application of driving signals in both cases.

The above-mentioned wavelength-variable light outputting apparatus can be applied not only to the fluorescent image capturing apparatus, but also to a transmitted or absorbed light image capturing apparatus for yielding a sample image reflecting a sample-constituting material if the sample image is captured at variable wavelengths. The images obtained at these plurality of wavelengths can be combined by the control unit 15 shown in FIG. 3, so as to be displayed on the display 18.

As explained in the foregoing, the above-mentioned wavelength-variable light outputting apparatus comprises the light source 1 outputting light having a plurality of wavelengths, the swinging first galvanometric scanner 12 provided with the spectroscopic means 8 for spectrally dividing the light outputted from the light source 1, the swinging second galvanometric scanner 13 provided with the shielding member 11 or reflecting member 11' adapted to block or reflect at least a part of light outputted from the spectroscopic means 8, and the optical fiber 10 disposed at a position where light outputted from the spectroscopic means 8 can be made incident by way of the shielding or reflecting member 11, 11'.

The light outputted from the light source 1 is fed into spectroscopic means 8 such as a diffraction grating or prism. Since the spectroscopic means 8 spectrally divides the light outputted from the light source 1, the emitting direction of a specific wavelength component among thus divided light components can be deflected by swinging the first galvanometric scanner 12. This specific wavelength component is made incident on the shielding member 11 or reflecting member 11', whereby a part thereof is blocked or reflected. Since such a member is provided with the second galvanometric scanner 13, the transmission light quantity or reflecting direction of the specific wavelength component is variable when the second galvanometric scanner 13 is swung.

Since the optical fiber 10 is disposed at a position where light outputted from the spectroscopic means 8 can be made incident by way of the shielding or reflecting member 11, 11', the quantity of light finally incident on the optical fiber 10 can vary if the transmission light quantity is made variable by the shielding member 11 whereas, due to the fact that the input end face F of the optical fiber 10 has a core with a finite diameter, the quantity of light finally entering the core of the optical fiber 10 will vary if the reflecting direction is made variable by the reflecting member 11'.

Thus, since the galvanometric scanners 12, 13, which can swing at a high speed are provided with the spectroscopic means 8 and the shielding or reflecting member 11, 11', respectively, the above-mentioned wavelength-variable light outputting apparatus can select a specific wavelength component at a high speed and make its light quantity variable at a high speed. As mentioned above, such an apparatus is useful for capturing a fluorescent image of the biological sample SM. By way of the shielding member 11, light is made incident on the optical fiber 10 and is outputted therefrom, whereby the biological sample SM can effectively be irradiated with light.

The present invention can provide a wavelength-variable light outputting apparatus which can make wavelengths variable at a high speed while controlling light quantities.

INDUSTRIAL APPLICABILITY

The present invention can be utilized in a wavelength-variable light outputting apparatus for irradiating an object with light whose wavelength is made variable.

What is claimed is:

1. A wavelength-variable light outputting apparatus comprising:
    a light source outputting light having a plurality of wavelengths;
    a swinging first galvanometric scanner provided with spectroscopic means for spectrally dividing said light outputted from said light source;
    a swinging second galvanometric scanner provided with a shielding or reflecting member adapted to block or reflect at least a part of light outputted from said spectroscopic means, wherein said swinging first and second galvanometric scanners have swinging axes that extend in different directions from each other;
    an optical fiber disposed at a position where light outputted from said spectroscopic means can be made incident by way of said shielding or reflecting member; and
    a control unit that controls said swinging first and second galvanometric scanners, said swinging second galvanometric scanner being controlled so as to control a quantity of light incident on said optical fiber, the quantity of light incident on the optical fiber varying in accordance with the transmission or reflection of light by said shielding or reflecting member, respectively.

2. A wavelength-variable light outputting apparatus according to claim 1, comprising:
    storage means for storing respective swinging angles of said first and second galvanometric scanners and a relationship between wavelength and quantity of light outputted from said optical fiber in response to a combination of said swinging angles;
    input means for inputting information concerning wavelength and quantity of light to be outputted from said optical fiber; and said control means reading out said relationship from said storage means according to said information fed into said input means and controlling said swinging angles of said first and second galvanometric scanners in response to said relationship.

3. A wavelength-variable light outputting apparatus according to claim 1, said control means changing a wavelength of light outputted from said optical fiber by changing a swinging angle of said first galvanometric scanner and changing a swinging angle of said second galvanometric scanner such that the quantity of said wavelength of light fed to said shielding or reflecting member in response to said swinging angle of said first galvanometric scanner and the ratio of incidence of light incident on said optical fiber in response to said swinging angle of said second galvanometric scanner form a fixed product therebetween.

4. A wavelength-variable light outputting apparatus according to claim 1,
    wherein said shielding or reflecting member partially blocks or reflects the light from said spectroscopic means.

5. A wavelength variable light outputting apparatus according to claim 1, wherein said swinging first and second galvanometric scanners have swinging axes that extend in different directions that are substantially perpendicular to each other.

6. A wavelength variable light outputting apparatus according to claim 1, wherein said swinging second galvanometric scanner is controlled so as to continuously control the quantity of light incident on said optical fiber.

* * * * *